United States Patent

Hansen et al.

[11] Patent Number: 5,366,372
[45] Date of Patent: Nov. 22, 1994

[54] METHOD AND APPARATUS FOR DEBONDING CERAMIC ORTHODONTIC BRACKETS

[75] Inventors: James D. Hansen, Duarte; Evangelos G. Georgakis, Altaloma, both of Calif.

[73] Assignee: Minnesota Mining and Manufacturing Company, St. Paul, Minn.

[21] Appl. No.: 158,709

[22] Filed: Nov. 29, 1993

[51] Int. Cl.⁵ .............................................. A61C 3/00
[52] U.S. Cl. ........................................... 433/4; 433/9
[58] Field of Search .................. 433/2, 3, 4, 9, 159, 433/160

[56] References Cited

U.S. PATENT DOCUMENTS

| | | | |
|---|---|---|---|
| 3,986,265 | 10/1976 | Cusato | 433/9 |
| 4,043,364 | 8/1977 | Rose | 433/159 |
| 4,216,583 | 8/1980 | Reynolds | 433/9 |
| 4,219,617 | 8/1980 | Wallshein | 433/8 |
| 4,248,587 | 2/1981 | Kurz | 433/4 |
| 4,256,455 | 3/1981 | Forster | 433/9 |
| 4,533,932 | 11/1985 | Armstrong et al. | 433/4 |
| 4,639,218 | 1/1987 | Jones et al. | 433/8 |
| 4,681,538 | 7/1987 | DeLuca et al. | 433/9 |
| 4,776,791 | 10/1988 | Hannla et al. | 433/4 |
| 4,904,183 | 2/1990 | Hannan et al. | 433/3 |
| 4,950,157 | 8/1990 | Cleary | 433/4 |
| 4,954,080 | 9/1990 | Kelly et al. | 433/8 |
| 5,098,288 | 3/1992 | Kesling | 433/9 |
| 5,256,062 | 10/1993 | Griott | 433/9 |
| 5,263,859 | 11/1993 | Kesling | 433/9 |

OTHER PUBLICATIONS

Transcend brochure, 3M Unitek Corporation, copyright 1988.

Primary Examiner—John J. Wilson
Attorney, Agent, or Firm—Gary L. Griswold; Walter N. Kirn; James D. Christoff

[57] ABSTRACT

An orthodontic bracket having mesial and distal sections is debonded from a tooth by pivoting the sections toward each other in respective arcs about a central reference axis extending in an occlusal-gingival direction. The mesial and distal sections are discrete and spaced apart from each other, or alternatively integrally joined by a relatively thin web that bends and optionally fractures upon debonding. A metallic archwire slot liner interconnects the mesial and distal sections and enhances sliding mechanics of the bracket. A pliers-like debonding tool includes jaws with stops for limiting the lingual depth of engagement of the laws with the mesial and distal sides of the bracket, to facilitate pivoting of the mesial and distal sections during debonding.

15 Claims, 4 Drawing Sheets

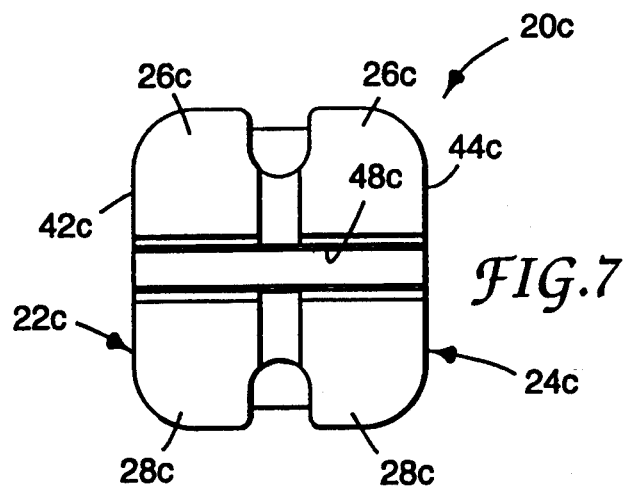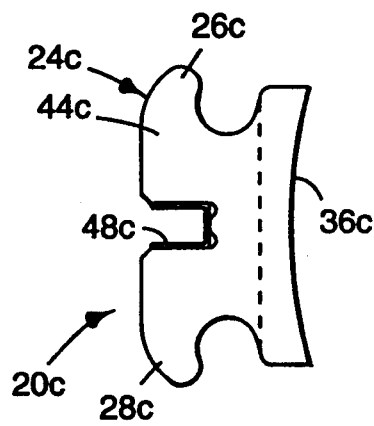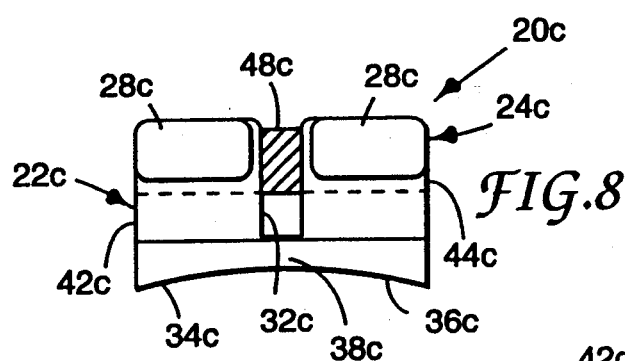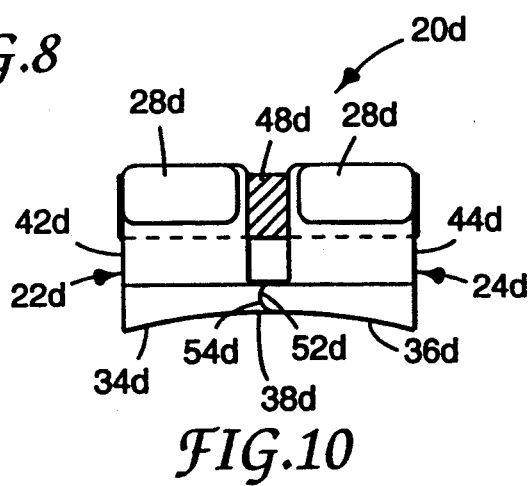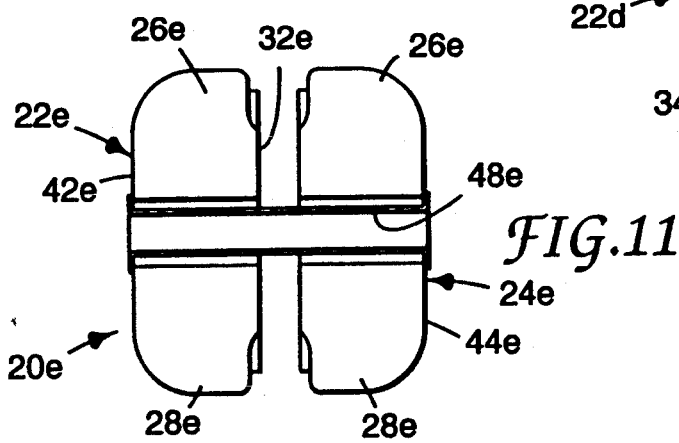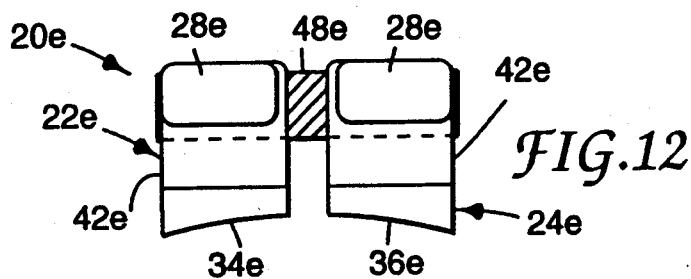

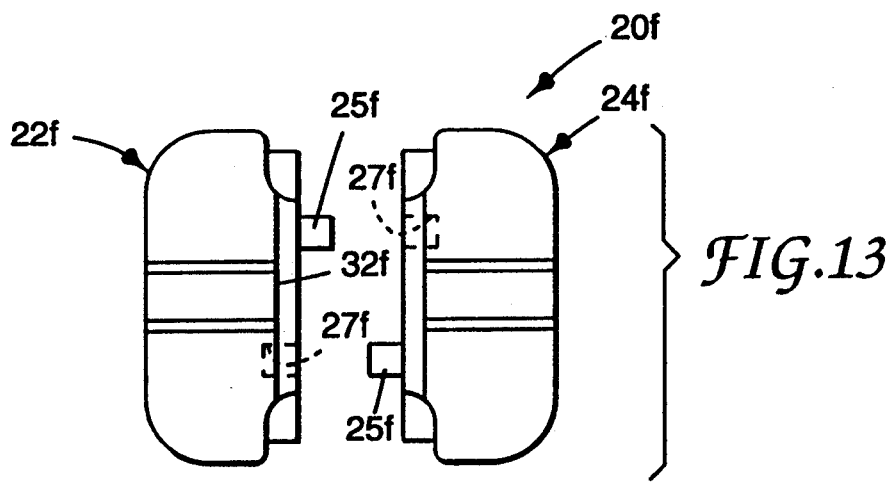
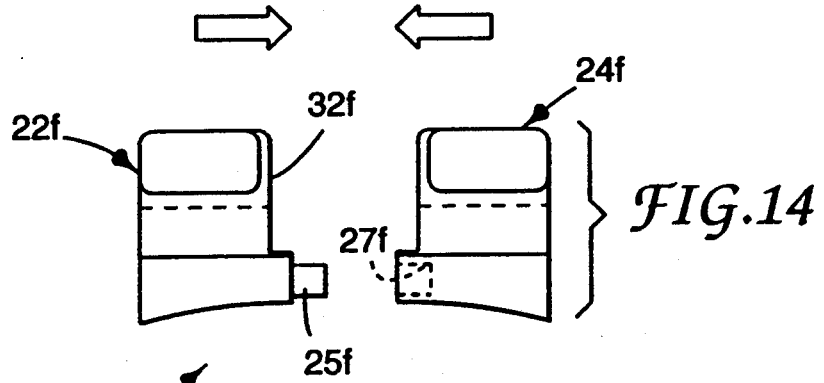
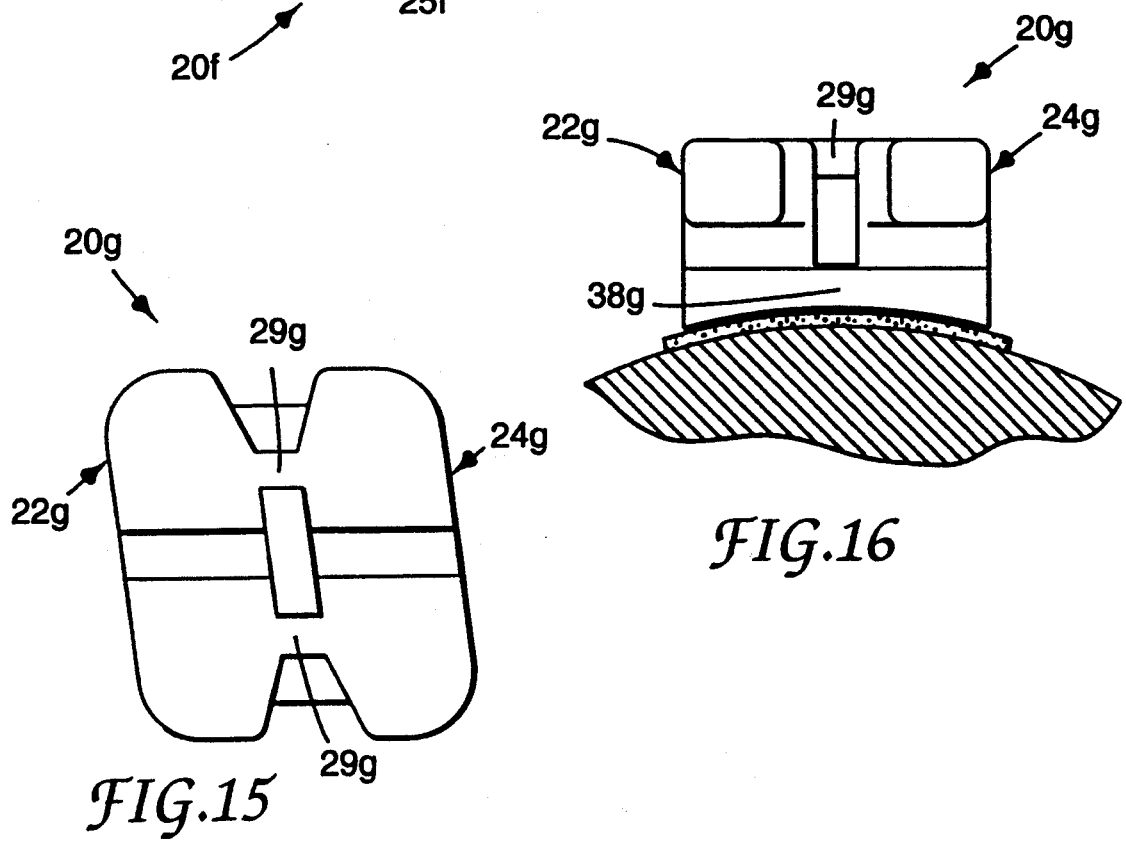

METHOD AND APPARATUS FOR DEBONDING CERAMIC ORTHODONTIC BRACKETS

BACKGROUND OF THE INVENTION

1. Field of the Invention

This invention relates to a method and apparatus for removing a ceramic orthodontic bracket from a tooth.

2. Description of the Related Art

Orthodontic treatment involves movement of the teeth toward positions for correct occlusion. During treatment, tiny orthodontic appliances known as brackets are connected to the teeth, and an archwire is placed in a slot of each bracket. The archwire forms a track to guide movement of the teeth to orthodontically correct positions.

Orthodontic brackets are typically made of metal, ceramic or plastic. Metal brackets are widely used and are considered by many orthodontists to have mechanical properties that are satisfactory for moving the teeth to desired positions. Unfortunately, metal brackets are not aesthetic in the mouth and often lead to comments of a "metallic mouth appearance" that can be an embarrassment to the patient.

Orthodontic brackets that are made of a plastic material are generally considered more aesthetic than metal brackets. However, some plastic brackets are stained by certain food and beverages and turn an unsightly color after a period of time. Moreover, the plastic material may slowly creep in use such that the archwire slot widens and precise control of tooth movement is hindered.

Orthodontic brackets that are made of transparent or translucent ceramic materials overcome many of the problems associated with plastic brackets, since ceramic material is resistant to staining and does not deform by creep as in the case with plastic brackets. U.S. Pat. No. 4,954,080, assigned to the assignee of the present invention, describes a color-free ceramic bracket made of polycrystalline material with a translucency that permits the natural color of the tooth to diffusely show through the bracket. An improved translucent polycrystalline ceramic bracket having a metallic archwire slot liner to enhance sliding movement of the bracket on the archwire is described in pending U.S. application Ser. Nos. 08/061,215 and 08/061,164, both of which were filed on May 13, 1993.

In the past, orthodontic brackets were commonly secured to bands that were placed around the teeth. Today, orthodontic brackets are often bonded directly to the surface of the teeth. Once treatment has been completed, the archwire is removed from the slot of the brackets and each bracket is then removed from the associated tooth.

Metal brackets are typically debonded by using a peeling or prying motion. U.S. Pat. Nos. 3,986,265 and 4,248,587 describe plier-type hand instruments that are used with a prying action to remove orthodontic brackets. U.S. Pat. No. 4,553,932, assigned to the assignee of the present invention, describes an peeling-type debonding tool having a pull wire with a loop for hooking a wing of the bracket and applying a pulling force to a tiewing located on one side of the bracket while a pair of spaced apart abutments engage the tooth on opposite sides of the bracket.

Peeling-type debonding methods are usually considered satisfactory for detaching brackets made of ductile materials such as metal. Debonding of such brackets often begins by fracturing the adhesive bond along one side of the bracket base, and then peeling or bending the base of the bracket so that the fracture propagates to remaining regions of the adhesive bond. In this manner, the debonding force is applied only to a relatively small, generally linear area at any particular point in time.

However, ceramic orthodontic brackets are relatively hard and brittle, and do not bend or flex like metal brackets during debonding. As a result, debonding occurs by fracturing the adhesive bond in all areas at essentially the same time, rather than in a propagating type of fracture as occurs when metal brackets are debonded by a peeling-type motion. Pulling on the tiewings of a ceramic bracket is not normally recommended because the ceramic material is brittle and the tiewings may break from remaining portions of the bracket.

Damage to the tooth structure may result during a debonding operation when excessive stress is applied to the tooth during attempts to lift or pry the bracket from the tooth. Tooth damage is more likely to occur when the tooth structure is weakened or has been previously damaged; however, such weakened or previously damaged tooth structure often cannot be noted by visual observation. Consequently, it is desirable that brackets are removed from the teeth with as little force as possible to minimize the risk of damage to the tooth.

It has been proposed in the past to weaken the strength of the bond between a ceramic bracket and the tooth so that debonding of the bracket is facilitated. However, such a solution is not entirely satisfactory because of the resulting increased likelihood that the bracket may unintentionally, prematurely debond during treatment. For example, a relatively weak adhesive may not have sufficient strength to resist debonding the bracket when the bracket is subjected to relatively large forces, as when the patient bites into a relatively hard food object. In other instances, a bracket may debond from forces exerted by the archwire or orthodontic auxiliaries or attachments coupled to the bracket. Premature debonding of orthodontic brackets represents a nuisance to both the orthodontist and the patient that is best avoided, since the detached bracket is normally re-bonded or replaced with a new bracket to finish treatment.

There is a need in the art for a ceramic bracket that provides the aesthetic advantages of ceramic material and functions similar to a metal bracket insofar as sliding mechanics are concerned, and yet is relatively easy to debond from the tooth surface. There is also a need in the art for a new method of debonding ceramic orthodontic brackets, and a hand instrument that facilitates debonding of such brackets.

SUMMARY OF THE INVENTION

The present invention concerns a method of debonding a ceramic orthodontic bracket from a tooth that comprises the step of engaging mesial and distal sides of the bracket in areas located buccolabially of a base of the bracket. The method also includes the step of urging the engaged mesial and distal sides toward each other in order to pivot at least one of a mesial section and a distal section of the bracket away from underlying areas of the tooth and about an axis generally parallel to a longitudinal axis of a channel that extends in a generally occlusal-gingival direction between the mesial and distal sections of the bracket.

Another aspect of the invention is directed toward orthodontic apparatus that comprises an orthodontic bracket having a mesial section with a mesial side, a distal section with a distal side and an archwire slot extending in a generally mesial-distal direction. The bracket includes a channel that extends in a generally occlusal-gingival direction between the mesial section and the distal section. The apparatus also includes a debonding tool having a pair of opposed jaws, a pair of handles each connected to one of the jaws and a coupling for connecting the handles to each other. The coupling enables movement of the jaws toward each other as the handles are moved toward each other. Each of the jaws includes a wall for engaging one of the sides of the bracket. Each of the jaws includes a stop for limiting the depth in a lingual direction of engagement of the respective wall with the side of the bracket.

The present invention is also directed to an orthodontic bracket debonding tool for debonding an orthodontic bracket having a labial side, a mesial section with a mesial side, a distal section with a distal side, and a slot extending in a generally mesial-distal direction in the mesial section and the distal section for receiving an archwire. The tool comprises a pair of opposed jaws and a pair of handles, each handle being connected to one of the jaws. A coupling movably connects the handles to each other and enables movement of the jaws toward each other as the handles are moved toward each other. The jaws each include an outer end portion having a wall for engaging mesial or distal sides of the bracket, a stop for engaging a labial side of the bracket and a groove extending through the wall for straddling an archwire received in a slot of the bracket.

BRIEF DESCRIPTION OF THE DRAWINGS

FIG. 7 is an elevational view of an orthodontic bracket according to another embodiment of the invention, looking toward a labial side of the bracket;

FIG. 8 is a bottom view looking toward a gingival side of the bracket shown in FIG. 7;

FIG. 9 is an elevational view of the bracket depicted in FIGS. 7-8, looking toward a mesial side of the bracket;

FIG. 10 is a view somewhat similar to FIG. 8, but in accordance with another embodiment of the invention;

FIG. 11 is a view somewhat similar to FIG. 7, but according to yet another embodiment of the invention;

FIG. 12 is a bottom view looking toward a gingival side of the bracket shown in FIG. 11;

FIG. 13 is an exploded elevational view looking toward a labial side of a bracket according to another embodiment of the invention;

FIG. 14 is a bottom exploded view looking toward a gingival side of the bracket shown in FIG. 13;

FIG. 15 is an elevational view looking toward a labial side of a bracket in accordance with another embodiment of the invention;

FIG. 16 is a bottom view looking toward a gingival side of the bracket of FIG. 15 along with a tooth upon which the bracket is bonded;

DETAILED DESCRIPTION OF THE PREFERRED EMBODIMENTS

Figure 1:
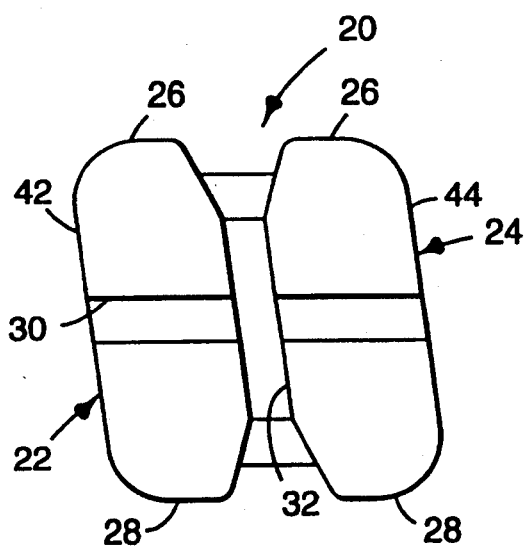
FIG. 1 is an elevational view looking toward a labial side of an orthodontic bracket made in accordance with one embodiment of the invention.
Figure 2:
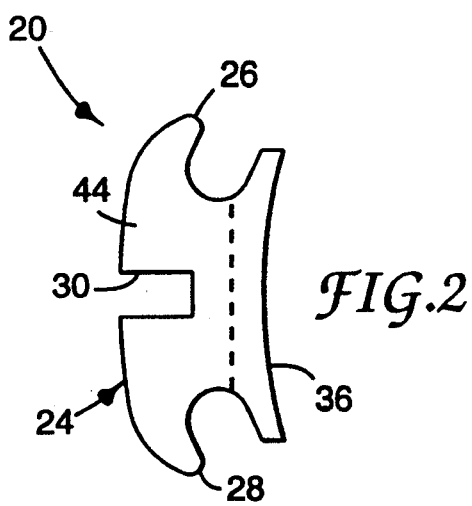
FIG. 2 is an elevational view of the bracket shown in FIG. 1, looking toward a mesial side of the bracket.
Figure 3:
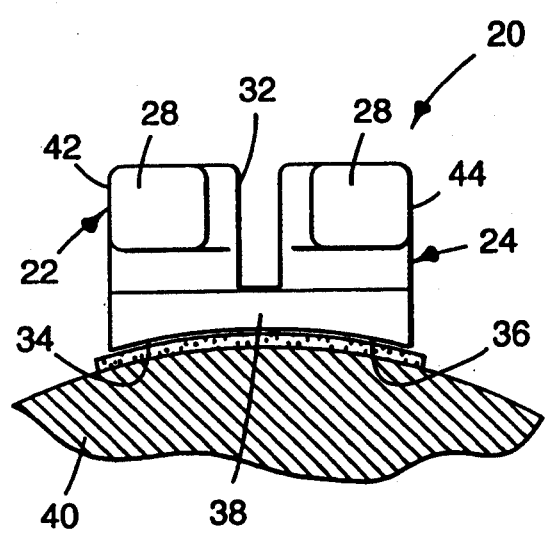
FIG. 3 is a bottom view of the bracket shown in FIGS. 1-2, looking toward a gingival side of the bracket and showing, for illustrative purposes, the surface of a tooth upon which the bracket is mounted.

Referring initially to FIGS. 1-3, a ceramic orthodontic bracket 20 according to one embodiment of the invention is illustrated and includes a mesial (i.e., facing toward the middle of the dental arch) section 22 and a distal (i.e., facing away from the middle of the dental arch) section 24. The mesial and distal sections 22, 24 each include an occlusal (i.e., toward the outer tip of the tooth) tiewing 26 and a gingival (i.e., adjacent the gingiva or gum) tiewing 28 that extend over ligature-receiving undercuts or grooves of the bracket 20.

An archwire slot 30 extends in a generally mesial-distal direction in the mesial section 22 and the distal section 24, and preferably has spaced apart, parallel occlusal and gingival walls interconnected by a perpendicular bottom wall and positioned to matingly receive an archwire having a rectangular cross-section for treatment according to the orthodontic technique known as the edgewise technique.

The bracket 20 includes a channel 32 that extends in a generally occlusal-gingival direction between the mesial section 22 and the distal section 24. As can be observed by comparing FIG. 3 with FIG. 2, the channel 32 has a depth in a lingual (i.e., toward the tongue) direction that is greater than the lingual depth of the archwire slot 30. The channel 32 in this embodiment has a rectangular configuration in transverse cross-section and extends from the occlusal side to the gingival side of the bracket 20.

The mesial section 22 includes a base having an external lingual surface for bonding the bracket 20 to a tooth. Likewise, the distal section 24 has a base with an external lingual surface 36 for bonding the bracket 20 to a tooth.

The base of the mesial section 22 and the base of the distal section 24 are integrally connected by a thin, frangible web 38 that extends directly beneath and along the entire length of the debonding channel 32. Optionally, the channel 32 has a rounded bottom to enhance fracturing of the web 38 along the central, longitudinal axis of the channel 32. As can be observed by reference to FIG. 3, an external lingual surface of the web 38 smoothly interconnects the bonding surfaces 34, 36 of the mesial and distal sections 22, 24, and the three surfaces together present a concave, compoundly curved configuration that matches the convexly curved shape of a surface of a tooth 40 to which the bracket 20 is adhesively bonded.

When the orthodontist desires to remove the bracket 20 from the tooth 40 (FIGS. 3 and 4), a pliers-type tool, and preferably the debonding tool described herein below, is used to fracture the adhesive bond between the bracket 20 and the tooth 40. To this end, one jaw of the pliers-like debonding tool is placed in a position to engage a mesial side 42 of the mesial section 22 next to the occlusal tiewing 26 and the gingival tiewing 28, while the remaining jaw is placed to engage a distal side 44 of the distal section 22 in areas adjacent the occlusal tiewing 26 and the gingival tiewing 28. The jaws engage the sides 42, 44 in buccolabial (i.e., toward the cheeks or lips) areas of the sections 22, 24, and preferably do not engage those portions of the sections 22, 24 that are located lingually of the bottom of the debonding channel 32.

Figure 4:
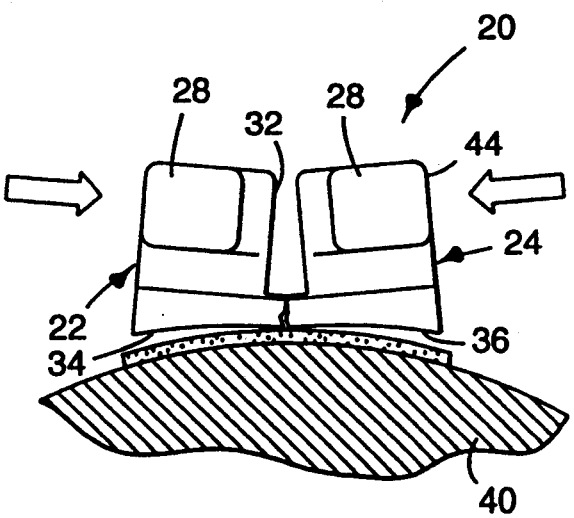
FIG. 4 is a view somewhat similar to FIG. 3 except that mesial and distal sections of the bracket have been pivoted toward one another in order to debond the bracket from the tooth.

Next, the engaged mesial and distal sides 42, 44 are urged toward each other in such a manner that one or both of the sections 22, 24 pivot in direction(s) toward each other in an arc and about a reference axis that is generally parallel to the longitudinal, occlusal-gingival axis of the debonding channel 32. As one or both of the sections 22, 24 pivot from the orientations as shown in FIG. 3 and toward the orientations as shown in FIG. 4, the web 38 fractures in the manner illustrated in FIG. 4, thereby enabling the bonding surfaces 34, 36 to detach from underlying areas of the tooth 40.

The channel 32 greatly facilitates debonding of the bracket 20 from the tooth 40 because the pivotal or rocking motion is believed to concentrate the debonding stresses in an effective manner along outer, mesial and distal edges of the bracket base. It is believed that such stresses are significantly lower than the stresses that are needed to debond, for example, a ceramic bracket of similar size using a tensile force in directions perpendicularly away from the tooth surface. As a consequence, the pivoting debonding motion should reduce the likelihood of injury to the enamel surface of the underlying tooth 40.

The bracket 20 is preferably made of a translucent, polycrystalline ceramic material exhibiting light transmittance sufficient for the bracket 20 to assume the color of the underlying tooth. Suitable ceramic materials are described in U.S. Pat. No. 4,954,080, the disclosure of which is incorporated by reference herein. Other ceramics may also be used, such as monocrystalline alpha-alumina, porcelain, glass, glass-ceramics and the like.

The buccolabial thickness of the web 38 is preferably less than about 0.030 in. (0.7 mm) and preferably is about 0.015 in. (0.4 mm). The mesiodistal width of the channel 32 may be a relatively small dimension, such as 0.001 inc. (0.02 mm), that is sufficient to enable the mesial and distal sections 22, 24 to rock in an arc sufficient to debond from the tooth. Alternatively, the mesiodistal width of the debonding channel 32 is of a larger dimension, such as 0.07 in. (1.8 mm), that is sufficient to enable the channel 32 to receive a conventional ligature when tied only about one of the sections 22, 24 for tooth rotation, and thereby enable the bracket 20 to function as a twin bracket.

Preferably, the mesiodistal width of the channel 32 is about 0.02 in. (0.5 mm), which is sufficient for the channel 32 to receive auxilliary appliances while the bracket 20 is bonded to a tooth. Such construction also enables the bracket 20 to function as a twin bracket, while maintaining sufficient tiewing width for satisfactory tiewing strength.

Optionally, the debonding channel 32 is filled with a compliant material such as a flexible plastic material in all areas except where the archwire passes through the debonding channel 32. Such construction is an advantage in those instances where the orthodontist does not desire to use the bracket 20 as a twin bracket and wishes to avoid unneeded recesses or cavities in the bracket that might otherwise trap food or bacteria. The compliant material is sufficiently compressible to enable the mesial and distal sections 22, 24 to be rocked toward each other without undue hindrance during debonding.

Figure 5:
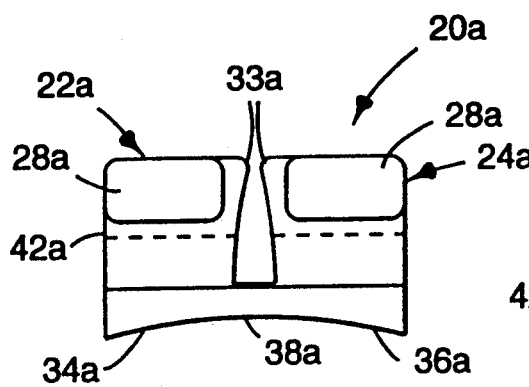
FIG. 5 is a bottom view looking toward a gingival side of a ceramic orthodontic bracket according to another embodiment of the invention.

A bracket 20a illustrated in FIG. 5 is another embodiment of the invention that is somewhat similar to the embodiment illustrated in FIGS. 1–4. Unless otherwise mentioned, the elements in FIG. 5 bearing numbers similar to the numbers in FIGS. 1–4 are the same as the elements in FIGS. 1–4 and as a result a detailed description of such elements shall not be repeated. However, and as can be appreciated by viewing FIG. 5, the bracket 20a has a debonding channel 32a with a different configuration than the debonding channel 32 described in connection with FIGS. 1–4.

More particularly, the debonding channel 32a in FIG. 5 has opposed walls that are inclined toward each other as the labial side of the bracket 20a is approached. The walls of the channel 32a include stop portions 33a near the labial side of the bracket 20a that face each other. As can be observed, the distance in FIG. 5 between the stop portions 33a is smaller than the mesial-distal width of the bottom of the channel 32a.

As the mesial side 22a and the distal side 24a are pivoted toward each other to debond the bracket 20a from the surface of the tooth, the web 38a bends slightly and the stop portions 33a come into contact with each other. The initial, relatively small distance between the stop portions 33a is sufficiently large to enable the web 38a to flex for debonding the bracket 20, but is small enough to preclude the web 38a from bending to such a degree that the web 38a fractures. Such construction increases the likelihood that the bracket 20a remains as a one-piece assembly during the debonding operation, and thereby reduces the likelihood that one of the sections 22a, 24a will unintentionally fall in the mouth and be aspirated or swallowed.

Figure 6:
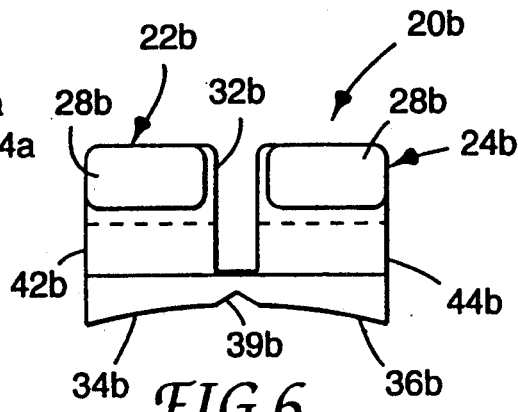
FIG. 6 is a view somewhat similar to FIG. 5 but in accordance with another embodiment of the invention.

The embodiment of the invention that is illustrated in FIG. 6 concerns a bracket 20b that is somewhat similar to the bracket 20 illustrated in FIGS. 1–4. Unless otherwise mentioned, elements of the bracket 20b bearing numerals corresponding to the numbered elements of FIGS. 1–4 are similar and consequently will not be described again in detail.

In FIG. 6, however, the web 38b includes a recess 39b that extends from the occlusal side to the gingival side of the bracket 20b directly below the bottom of the debonding channel 32b. The recess 39b has a V-shaped bottom surface that extends in a buccolabial direction away from adjacent regions of the bonding surfaces 34b, 36b of the mesial section 22 and the distal section 24b. The recess 39b thus interrupts the continuity of the smoothly curved, convex shape of the adjacent bonding surfaces 34b, 36b and reduces the labial-lingual depth of the web 38b at its narrowest section in contrast to the embodiments shown in FIGS. 1–5. When the bracket 20b is debonded, the recess 39b facilitates concentration of stresses along the longitudinal, central axis of the web 38b, such that in all likelihood the bracket 20b will fracture along the narrowest section of the web 38b while other portions of the bracket 20b do not fracture and instead remain intact.

In the embodiment shown in FIGS. 7-9, a bracket 20c is again somewhat similar to the bracket 20 described in connection with FIGS. 1-4, and the numerals in FIGS. 7-9 refer to elements that are substantially identical to the elements bearing corresponding numerals in FIGS. 1-4 except as explained in the paragraphs that follow.

The bracket 20c includes an elongated, one-piece metallic archwire slot liner 48c that extends across the mesial section 22c and the distal section 24c. As illustrated in FIG. 9, the liner 48c has a rectangular configuration in transverse cross-section to receive a rectangular archwire in mating relation. The mesial section 22c and the distal section 24c each have a mesiodistally extending slot of sufficient dimensions to receive the archwire slot liner 48c.

Preferably, the archwire slot liner 48c is made of type 303 stainless steel having a thickness of 0.002 in. (0.05 mm). Preferably, the archwire slot liner 48c is brazed to the mesial and distal sections 22c, 24c and the difference in the thermal coefficients of expansion enable the liner 48c to impose compressive forces on the sections 22c, 24c when the bracket 20c is cooled after the brazing operation. Additional details regarding the brazing process and other information regarding the archwire slot liner 48c, as well as other embodiments of the archwire slot liner 48c, are set out in pending U.S. patent applications Ser. Nos. 08/061,164 and 08/061,215.

When the bracket 20c is debonded from a tooth by urging the mesial and distal sections 22c, 24c toward each other, the archwire slot liner buckles to a somewhat crushed shape in areas of the debonding channel 32c. Advantageously, the archwire slot liner 48c is securely fixed to the mesial and distal sections 22c, 24c, and thus retains the sections 22c, 24c together during and after a debonding operation to facilitate removing the bracket 20c from the mouth in one piece. The archwire slot liner 48c also enhances sliding motion of the bracket 20c along the archwire.

A bracket 20d as shown in FIG. 10 is somewhat similar to the bracket 20c shown in FIGS. 7-9, except that a mesial section 22d and a distal section 24d are made as discrete units and are not integrally connected together. The bracket 20d does not have a single web that integrally interconnects the sections 22d, 24d in a manner similar to the web 38c, but instead has a two-part web 38d that includes an elongated tab 52d that is integrally connected to the base of the distal section 24d, and a groove 54d that is integrally connected to the base of the mesial section 22d. The tab 52d and the groove 54d provide registration structure that facilitates retaining the mesial and distal sections 22d, 24d together in a proper, abutting orientation before and during orthodontic treatment.

The tab 52d and the groove 54d have mating convex and concave configurations respectively, and extend the entire occlusal-gingival distance of the bracket 20d below the debonding channel 32d. Optionally, a thin layer of adhesive is applied to the interengaged surfaces of the tab 52d and the groove 54d to assist in retaining the mesial and distal sections 22d, 24d together during initial handling of the bracket 20d and during such time that the bracket 20d is used in therapy. The adhesive bond, however, is sufficiently weak to provide a fracture path for the web 38d that is parallel to the longitudinal axis of the channel 32d when debonding the bracket 20d. A suitable adhesive bond is made by applying a glass frit to the tab 52d and the groove 54d before assembly, and then firing the assembled sections 22d, 24d to melt the glass and thereby bond the sections 22d, 24d together.

FIGS. 11 and 12 illustrate a bracket 20e according to another embodiment of the invention that is somewhat similar to the bracket 20d shown in FIG. 10. However, the bracket 20e as shown in FIGS. 11 and 12 have mesial and distal sections 22e, 24e that are spaced apart from each other and interconnected with one another only by the archwire slot liner 48e. As such, the debonding channel 32e extends from the labial side of the bracket 20e to the bonding surfaces 34e, 36e.

The embodiments illustrated in FIG. 10 and FIGS. 11-12 provide a manufacturing advantage, especially when a dry pressing technique is utilized to make the brackets 20d, 20e. The mesial sections 22d, 22e and the distal sections 24d, 24e may be separately pressed in directions along a mesial-distal axis rather than along a labial-lingual axis as is commonly used when dry pressing conventional, one-piece ceramic brackets. By pressing the sections separately, relatively complex design features, such as slots to receive the archwire slot liner and grooved, undercut regions below the tiewings can be pressed in the green parts, rather than being machined in a secondary operation. Optionally, grit or glass may be added to the base surfaces 34d–e, 36d–e to enhance bonding of the brackets 20d–e directly to a tooth.

Further, in some instances, the mesial section and the distal section in the embodiments shown in FIGS. 10 and 11-12 may be identical, such that a single mold or die can be used to make both sections. In such an instance, it is preferred to replace the compound curved bonding surfaces of the mesial and distal sections with generically curved surfaces that are oriented to approximate the orientation of the underlying tooth surface, and use an orthodontic adhesive with sufficient strength to overcome the resulting lack of a precise, matching configuration between the compound curve of the external tooth surface and the bracket base. Optionally, the slot liner may be curved along its length in the labial-lingual/mesial-distal plane to enhance the fit between the tooth surface and the bracket base.

FIGS. 13-14 depict a bracket 20f according to another embodiment of the invention. The bracket 20f has a mesial section 22f and a distal section 24f that advantageously are identical and consequently reduce the costs of manufacture. Each self-mating section 22f, 24f includes a mesiodistally extending peg 25f that is received in a mating hole 27f of the other section 22f, 24f. Optionally, an adhesive is used to retain the pegs 25f in the holes 27f. As another alternative, bracket 20f may include a metal archwire slot liner to enhance sliding mechanics and also to assist in retaining the sections 22f, 24f together. During debonding, the pegs 25f break as the sections 22f, 24f are rocked toward each other about an occlusal-gingival debonding channel 32f.

FIGS. 15-16 illustrate a bracket 20g according to another embodiment of the invention. The bracket 20g is substantially similar to the bracket 20 shown in FIGS. 1-4, but includes a pair of spaced-apart bridges 29g that integrally interconnect mesial and distal sections 22g, 24g. The bridges 29g are spaced buccolabially from frangible web 38g and enhance the strength of the bracket 20g. However, bridges 29g are readily removed with a diamond burr prior to debonding: subsequently the sections 22g, 24g are pivoted toward each other about debonding channel 32g. (In this regard, it should be understood that bridges similar to bridges 29g may be used with the other brackets described above.

Figure 17:
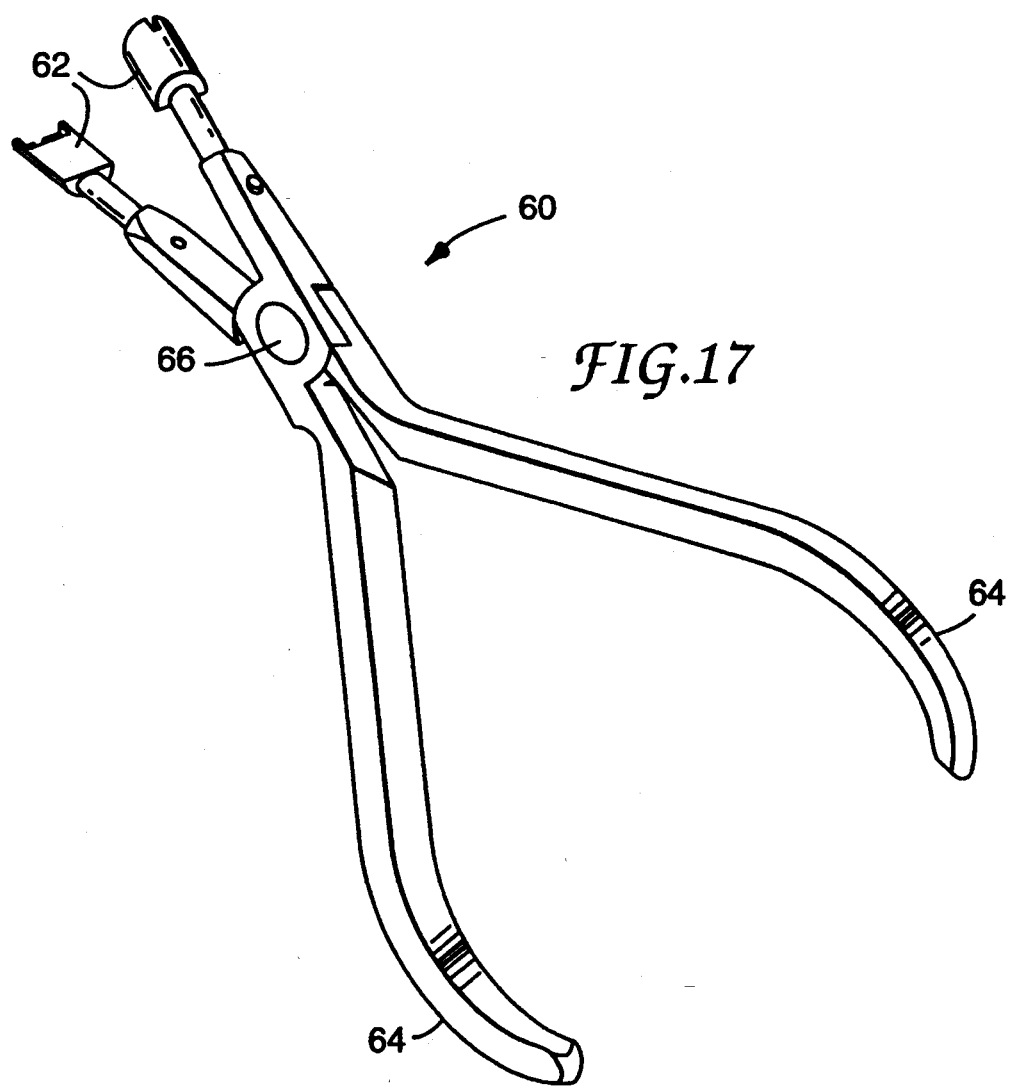
FIG. 17 is a perspective view of an orthodontic bracket debonding tool according to the invention.

An orthodontic debonding tool for debonding the brackets mentioned above is shown in FIGS. 17 and 18 and is designated by the numeral 60. The tool 60 is shown for illustrative purposes in FIG. 18 as used in connection with the bracket 20, but is also useful for debonding other brackets according to the invention such as brackets 20a-20e. The debonding tool 60 has a pliers-like configuration and includes a pair of opposed jaws 62 as well as a pair of handles 64.

Each of the handles 64 is connected to a respective one of the jaws 62, and the handles 64 and the jaws 62 are essentially identical. The handles are coupled together by a pivot 66 that enables the jaws 62 to move toward and away from each other as the handles 64 are moved toward or away from each other.

Each of the jaws 62 includes an outer end portion having a wall 68 for engaging either the mesial side 42 or the distal side 44 of the bracket 20. Each jaw 62 also includes a wall 70 oriented perpendicular to the wall 68, for engaging the labial surface of the bracket 20, or alternatively the labial side of an archwire 72 that is received in the archwire slot 30 of the bracket 20. A groove 74 extends through the wall 68 for straddling the archwire 72 in the manner shown in FIG. 18.

The walls 70 function as a stop to limit the lingual depth of engagement of the walls 68 with the respective mesial and distal sides 42, 44 of the bracket 20. Thus, when the handles 64 are squeezed together to close the jaws 62, the walls 68 apply compressive forces only to labial portions of the mesial and distal sections 22, 24 and not to base portions of the bracket 20 in areas lingually of the bottom of the debonding channel 32. Such construction facilitates rocking of the mesial and distal sections 22, 24 about the web 38 and helps insure that the web 38 will fracture in a direction along the longitudinal axis of the channel 32. Consequently, the probability is increased that the bracket 20 will fracture into only two pieces (i.e., the mesial and distal sections 22, 24) or, at most, three pieces (i.e., the sections 22, 24 and the web 38). The recessed walls 68, 70 advantageously serve as a trap in some instances during debonding when the archwire 72 has been removed, so that the broken pieces do not fall into the oral cavity.

Another advantage of the present invention is that a set of brackets 20 can be debonded from corresponding teeth in one arch of the mouth while all of such brackets 20 remain connected to the common archwire 72 by ligatures (not shown in FIG. 18) that are conventionally used during orthodontic treatment. The groove 74 enables the jaws 62 to be placed over the archwire 72 as well as the bracket 20 while enabling the ligature to remain in place to couple the bracket 20 to the archwire 72. The orthodontist can debond each bracket 20 in turn, and then lift the archwire 72 with all attached brackets 20 from the mouth. Such an advantage is important because less time is needed for debonding, and there is less likelihood that one or more of the brackets 20 will drop into the oral cavity and become ingested or aspirated during the debonding operation.

Figure 18:
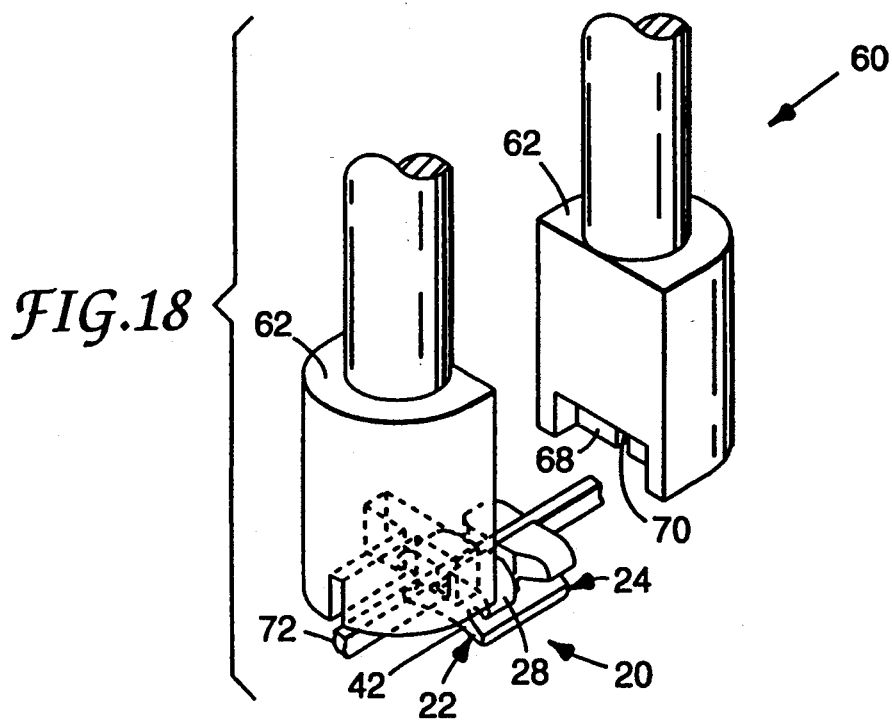
FIG. 18 is an inverted, enlarged, perspective, fragmentary view of one end of the tool shown in FIG. 17 along with an orthodontic bracket and an archwire received in a slot of the bracket, showing jaws of the tool being moved toward positions of engagement with the bracket for debonding the bracket from a tooth.

In the bracket 20 shown in FIG. 18, the archwire 72 is received in the archwire slot 30 to such a lingual depth that the labial side of the archwire 72 is located lingually of the labial side of the bracket 20. As such, the walls 70 engage the labial sides of the mesial and distal sections 22, 24 to limit the lingual engagement of the walls 68 with the mesial and distal sides 42, 44. As an alternative, the wall 70 may include a protruding portion for engaging the labial side of the archwire 72, or alternatively the archwire slot 30 of the bracket 20 may be located nearer the labial side of the bracket 20, so that engagement of the wall 70 with the archwire 72 serves to limit the depth of lingual engagement of the walls 68 on the mesial and distal sides 42, 44.

The debonding tool 60 is preferably made of a corrosion resistant 400 series stainless steel, such as type 420, that is suitable for repeated sterilization. As an alternative to the straight-line configuration of the tool 60 illustrated in FIGS. 17 and 18, the jaws may extend in a direction at an angle in the range of about 25 to 40 degrees relative to the major extent of the handles, to facilitate access to brackets bonded to posterior teeth.

We claim:

1. A method of debonding a ceramic orthodontic bracket from a tooth comprising the steps of:
   engaging a mesial side and a distal side of the bracket in areas located buccolabially of a base of the bracket; and
   urging the engaged mesial and distal sides toward each other in order to pivot at least one of a mesial section and a distal section of the bracket away from underlying areas of the tooth and about a reference axis generally parallel to a longitudinal axis of a channel that extends in a generally occlusal-gingival direction between the mesial section and the distal section of the bracket.

2. The method of claim 1, wherein said step of urging the mesial side and the distal side toward each other includes the step of fracturing a frangible web of the bracket that extends in a direction generally parallel to the longitudinal axis of the channel.

3. The method of claim 2, wherein said step of fracturing a web includes the step of breaking an adhesive bond between structure interconnecting the mesial section and the distal section in areas located lingually of the channel.

4. The method of claim 2, wherein said step of fracturing a web includes the step of fracturing a thin ceramic web that integrally interconnects the mesial section and the distal section in areas of the bracket lingually of the channel.

5. The method of claim 1, wherein said step of urging the mesial side and the distal side toward each other includes the step of buckling a metal liner that extends along an archwire slot of the bracket.

6. The method of claim 1, wherein said step of urging the engaged mesial side and distal side toward each other includes the step of compressing a compliant material located in the channel.

7. The method of claim 1, wherein said step of urging the engaged mesial and distal sides toward each other is carried out while an archwire is in engagement with the bracket.

8. Orthodontic apparatus comprising:
   a ceramic orthodontic bracket having a mesial section with a mesial side, a distal section with a distal side and an archwire slot extending in a generally mesial-distal direction, said bracket including a channel extending in a generally occlusal-gingival direction between said mesial section and said distal section; and
   a debonding tool having a pair of opposed jaws, a pair of handles each connected to one of said jaws and a coupling for connecting said handles to each other, said coupling enabling movement of said jaws toward each other as said handles are moved toward each other, each of said jaws including a wall for engaging one of said mesial and said distal sides of said bracket, each of said jaws including a stop for limiting the depth in a lingual direction of engagement of the respective wall with said mesial and said distal side of said bracket.

9. The apparatus of claim 8, wherein said bracket includes a labial side, and wherein said stop engages said labial side of said bracket.

10. The apparatus of claim 8, wherein said stop engages a labial side of an archwire when an archwire is received in said archwire slot of said bracket.

11. The apparatus of claim 8, wherein said walls each include a groove for straddling an archwire received in said archwire slot.

12. The apparatus of claim 8, wherein each of said jaws includes a recess, and wherein said wall is located in said recess.

13. An orthodontic bracket debonding tool for debonding an orthodontic bracket having a labial side, a mesial section with a mesial side, a distal section with a distal side, and a slot extending in a generally mesial-distal direction in said mesial section and said distal section for receiving an archwire, said tool comprising:

a pair of opposed jaws;

a pair of handles, each handle being connected to one said jaws; and a coupling movably connecting said handles to each other, said coupling enabling movement of said jaws toward each other as said handles are moved toward each other, said jaws each including an outer end portion having a wall for engaging the mesial side and the distal side respectively of the bracket, a stop for engaging the labial side of the bracket and a groove extending through the wall for straddling an archwire received in the slot of the bracket.

14. The hand tool of claim 13, wherein said coupling comprises a pivot that enables said jaws to move in an arc as said jaws move toward each other, and wherein said wall of each of said jaws is located in a reference plane generally perpendicular to said arc.

15. The hand tool of claim 13, wherein each of said jaws includes a recess, and wherein said wall of each of said jaws is located in said recess.

* * * * *

UNITED STATES PATENT AND TRADEMARK OFFICE
CERTIFICATE OF CORRECTION

PATENT NO. : 5,366,372

DATED : November 22, 1994

INVENTOR(S) : James D. Hansen and Evangelos G. Georgakis

It is certified that error appears in the above-indentified patent and that said Letters Patent is hereby corrected as shown below:

Abstract, line 12, "laws" should read -- jaws --.

Signed and Sealed this

Eighth Day of August, 1995

Attest:

BRUCE LEHMAN

Attesting Officer       Commissioner of Patents and Trademarks